(12) United States Patent
Jegou et al.

(10) Patent No.: US 11,633,346 B2
(45) Date of Patent: *Apr. 25, 2023

(54) COMPOSITION COMPRISING AT LEAST ONE ACRYLATE-FUNCTIONALIZED POLYMER AND AT LEAST ONE SILICONE CHOSEN FROM SILICONES FUNCTIONALIZED WITH AT LEAST ONE MERCAPTO OR THIOL GROUP

(71) Applicant: L'Oreal, Paris (FR)

(72) Inventors: Gwenaëlle Jegou, Aulnay-sous-Bois (FR); Eric Phalempin, Aulnay-sous-Bois (FR)

(73) Assignee: L'Oreal, Paris (FR)

( * ) Notice: Subject to any disclaimer, the term of this patent is extended or adjusted under 35 U.S.C. 154(b) by 759 days.

This patent is subject to a terminal disclaimer.

(21) Appl. No.: 16/307,453

(22) PCT Filed: Jun. 23, 2017

(86) PCT No.: PCT/EP2017/065544
§ 371 (c)(1),
(2) Date: Dec. 5, 2018

(87) PCT Pub. No.: WO2017/220781
PCT Pub. Date: Dec. 28, 2017

(65) Prior Publication Data
US 2019/0254954 A1    Aug. 22, 2019

(30) Foreign Application Priority Data
Jun. 24, 2016 (FR) ...................... 1655933

(51) Int. Cl.
| | | |
|---|---|---|
| *A61K 8/895* | (2006.01) | |
| *A61K 8/899* | (2006.01) | |
| *A61Q 5/12* | (2006.01) | |
| *A61K 8/898* | (2006.01) | |

(52) U.S. Cl.
CPC .............. *A61K 8/895* (2013.01); *A61K 8/898* (2013.01); *A61K 8/899* (2013.01); *A61Q 5/12* (2013.01); *A61K 2800/81* (2013.01); *A61K 2800/88* (2013.01); *A61K 2800/882* (2013.01); *A61K 2800/884* (2013.01); *A61K 2800/95* (2013.01)

(58) Field of Classification Search
None
See application file for complete search history.

(56) References Cited

U.S. PATENT DOCUMENTS

| | | |
|---|---|---|
| 5,166,276 A | 11/1992 | Hayama et al. |
| 5,807,543 A | 9/1998 | Coffindaffer et al. |
| 6,451,747 B1 | 9/2002 | Decoster |
| 2013/0164240 A1* | 6/2013 | Schrott .................. A61K 8/891 424/70.2 |
| 2015/0093422 A1 | 4/2015 | Baetzold |

FOREIGN PATENT DOCUMENTS

| | | |
|---|---|---|
| WO | 93/23446 A2 | 11/1993 |
| WO | 2015/061048 A1 | 4/2015 |

OTHER PUBLICATIONS

International Search Report dated Aug. 11, 2017, issued in corresponding International Application No. PCT/EP2017/065544, filed Jun. 23, 2017, 3 pages.

"Moisturizing Conditioner," Mintel online database, product information sheet for CHI Ionic Color Protector System from Farouk Systems, <www.gnpd.com>, Aug. 2010, 4 pages.

* cited by examiner

*Primary Examiner* — Nicole P Babson
(74) *Attorney, Agent, or Firm* — Christensen O'Connor Johnson Kindness PLLC

(57) ABSTRACT

Composition comprising at least one acrylate-functionalized polymer and at least one silicone chosen from silicones functionalized with at least one mercapto or thiol group The present invention relates to a composition intended for the cosmetic treatment of keratin fibres, in particular of human keratin fibres such as the hair, comprising one or more acrylate-functionalized polymers and one or more silicones chosen from silicones functionalized with one or more mercapto groups, amino silicones, and mixtures thereof.

13 Claims, No Drawings

COMPOSITION COMPRISING AT LEAST ONE ACRYLATE-FUNCTIONALIZED POLYMER AND AT LEAST ONE SILICONE CHOSEN FROM SILICONES FUNCTIONALIZED WITH AT LEAST ONE MERCAPTO OR THIOL GROUP

The present invention relates to a composition intended for the cosmetic treatment of keratin fibres, in particular of human keratin fibres such as the hair, comprising one or more acrylate-functionalized polymers and one or more silicones chosen from silicones functionalized with one or more mercapto groups, amino silicones, and mixtures thereof.

The invention also relates to a cosmetic process for treating keratin fibres, in which said fibres are treated with one or more compositions comprising one or more acrylate-functionalized polymers and one or more silicones chosen from silicones functionalized with one or more mercapto groups, amino silicones, and mixtures thereof.

Hair is generally damaged and embrittled by the action of external atmospheric agents such as light and bad weather, and also by mechanical or chemical treatments, such as brushing, combing, dyeing, bleaching, permanent-waving and/or relaxing.

Hair is thus damaged by these various factors and may over time become dry, coarse, brittle or dull, especially in fragile areas, and more particularly at the ends.

Thus, to overcome these drawbacks, it is common practice to resort to haircare products using compositions intended to condition the hair appropriately, giving it satisfactory cosmetic properties, especially in terms of smoothness, sheen, softness, suppleness, lightness, a natural feel and good disentangling properties. The purpose of these compositions is thus to protect, repair, and transform the hair cosmetically in a long-lasting manner.

These haircare compositions, intended to be applied regularly to the hair, may be, for example, conditioning shampoos, hair conditioners, masks or sera, and may be in the form of gels, hair lotions or care creams that are more or less thick.

However, such compositions lead all too often to effects that are not sufficiently long-lasting and which become attenuated especially on washing.

There is thus a real need to use on keratin fibres, in particular human keratin fibres such as the hair, compositions which do not have the drawbacks mentioned previously, i.e. which are capable of conditioning keratin fibres in a long-lasting manner, in particular giving them shampoo-resistant cosmetic properties.

This aim is achieved by the present invention, one subject of which is especially a composition comprising (i) one or more acrylate-functionalized polymers and (ii) one or more silicones chosen from silicones functionalized with one or more mercapto groups, amino silicones, and mixtures thereof.

The composition according to the invention makes it possible to condition keratin fibres satisfactorily, especially improving the disentangling and the soft feel, and doing so in a long-lasting manner.

Thus, the composition according to the invention makes it possible to give keratin fibres satisfactory and shampoo-resistant cosmetic properties.

In particular, the composition according to the invention makes it possible to afford improved disentangling and an improved soft feel, even after five shampoo washes, relative to a composition comprising an acrylate-functionalized polymer or a silicone functionalized with one or more mercapto groups.

Consequently, the keratin fibres may be protected, repaired and transformed cosmetically in a long-lasting manner.

A subject of the invention is also a cosmetic process for treating keratin fibres, in particular human keratin fibres such as the hair, in which said fibres are treated with one or more compositions containing, taken together or separately in said composition(s), the following ingredients:
  one or more acrylate-functionalized polymers,
  one or more silicones chosen from silicones functionalized with one or more mercapto groups, amino silicones, and mixtures thereof.

The process thus makes it possible to condition keratin fibres satisfactorily and in a long-lasting manner.

Another subject of the present invention concerns the use of the composition as defined previously for the conditioning of keratin fibres, in particular human keratin fibres such as the hair.

The invention also relates to a multi-compartment device comprising at least a first compartment containing a composition comprising one or more acrylate-functionalized polymers and a second compartment containing one or more silicones chosen from silicones functionalized with one or more mercapto groups, amino silicones, and mixtures thereof.

Other characteristics and advantages of the invention will emerge more clearly on reading the description and the examples that follow.

In that which follows and unless otherwise indicated, the limits of a range of values are included within this range, in particular in the expressions "of between" and "ranging from . . . to . . . ".

As indicated above, the composition according to the invention comprises (i) one or more acrylate-functionalized polymers, this acrylate-functionalized polymer being an acrylate polymer comprising a reactive acrylate function that is capable of reacting, this acrylate function being able to be represented by CH2=CH—C(=O)—O—R, R being a divalent radical linking the reactive acrylate function to the polymer backbone.

Preferably, this acrylate-functionalized polymer(s) being an acrylate polymer comprising a reactive acrylate function that is capable of reacting, this acrylate function is represented by CH2=CH—C(=O)—O—R, R being a divalent radical linking the reactive acrylate function to the polymer backbone.

More preferentially, the acrylate-functionalized polymer(s) is or are chosen from acrylate-functionalized polyesters, acrylate-functionalized polyurethanes and acrylate-functionalized silicone polymers.

More preferentially still, the acrylate-functionalized polymer(s) is or are chosen from acrylate-functionalized silicone polymers.

Throughout the text hereinbelow, the term "silicone" is intended to denote, in accordance with what is generally accepted, any organosilicon polymer or oligomer of linear or cyclic, branched or crosslinked structure, of variable molecular weight, obtained by polymerization and/or polycondensation of suitably functionalized silanes, and constituted essentially of a repetition of main units in which the silicon atoms are linked together via oxygen atoms (siloxane bond —Si—O—Si—), optionally substituted hydrocarbon-based radicals being directly linked via a carbon atom to said silicon atoms. The hydrocarbon-based radicals that are the most common are alkyl radicals, especially of $C_1$-$C_{10}$, and in particular methyl, fluoroalkyl radicals, the alkyl part of which is of $C_1$-$C_{10}$, and aryl radicals and in particular phenyl.

The acrylate-functionalized silicone polymer(s) comprise a polysiloxane portion and a portion constituted of a non-silicone organic chain comprising one or more acrylate reactive groups; the non-silicone portion being grafted onto said polysiloxane portion in a side or end position.

Thus, the portion constituted of a non-silicone organic chain comprising one or more acrylate reactive groups is grafted onto the main chain of the polymer constituted by the polysiloxane portion.

Preferably, the acrylate-functionalized silicone polymer(s) is or are chosen from acrylate-functionalized silicone homopolymers and acrylate-functionalized silicone copolymers.

More preferentially, the acrylate-functionalized silicone polymer(s) is or are chosen from acrylate-functionalized silicone copolymers, in particular copolymers comprising in their structure at least one acrylate-functionalized silicone unit and at least one dimethylsiloxane unit.

Preferably, the acrylate-functionalized silicone polymer(s) is or are a polymer of formula (I) or (II) below:

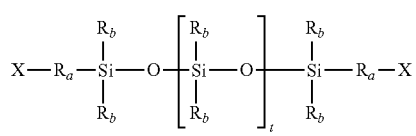

(I)

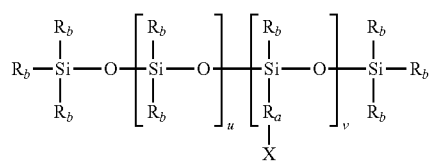

(II)

in which:

$R_a$ denotes a saturated or unsaturated, linear or branched, optionally cyclic, hydrocarbon-based chain comprising from 1 to 100 carbon atoms, optionally interrupted with a heteroatom chosen from N, O, S and P.

$R_a$ preferably denotes a $C_1$-$C_{100}$ alkylene group, better still a propylene group, $R_b$ denotes an alkyl group containing from 1 to 6 carbon atoms or an alkoxy group containing from 1 to 6 carbon atoms.

$R_b$ preferably denotes a methyl group or a methoxy group, t ranges from 0 to 132, and u ranges from 1 to 132, v ranges from 1 to 132, X represents an acrylate group.

According to a particular embodiment, X represents an acrylate group $R'_aO(C=O)C(R')=CH_2$ with $R'_a$ corresponding to a $C_1$-$C_{20}$ and preferably $C_1$-$C_5$ alkylene group, and R' represents a $C_1$-$C_{10}$ alkylene group.

In particular, the acrylate-functionalized silicone polymer(s) is or are a polymer of formula (III) below:

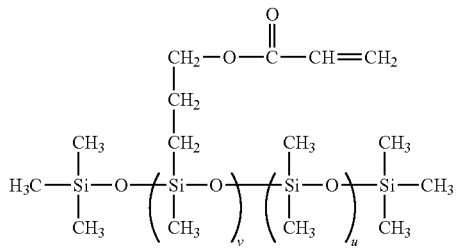

(III)

in which u and v have the same definition as those indicated in formulae (I) and (II) described previously.

Even more preferentially, the acrylate-functionalized polymer(s) is or are chosen from acryloxypropylmethylsiloxane polymers, especially the product sold under the trade name UMS-992 by the company Gelest, and copolymers of dimethylsiloxane and of acryloxypropylmethylsiloxane, especially the product sold under the trade name UMS-182R by the company Gelest.

Preferably, the acrylate-functionalized polymer is the polymer of formula (III) described previously comprising from 15 to 50 mol % of acryloxypropylmethylsiloxane.

The acrylate-functionalized polymer(s) may be present in the composition according to the invention in a content which may range from 0.1% to 20% by weight, preferably in a content ranging from 0.5% to 10% by weight relative to the total weight of the composition.

As indicated above, the composition according to the invention comprises (ii) one or more silicones chosen from silicones functionalized with one or more mercapto groups, amino silicones, and mixtures thereof.

Preferably, the silicone(s) (ii) is or are chosen from silicones functionalized with one or more mercapto groups.

Preferentially, the silicone(s) functionalized with one or more mercapto groups have a molecular weight preferably less than 1000.

The silicone(s) functionalized with one or more mercapto groups according to the invention may be chosen from the compounds having the following formulae:

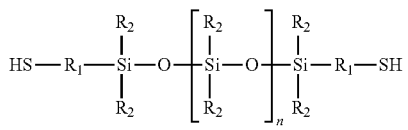

(XXIV)

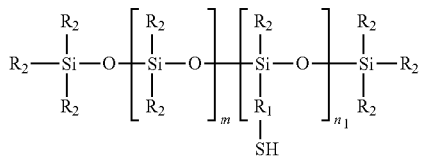

(XXV)

in which:

$R_1$ denotes a saturated or unsaturated, linear or branched, optionally cyclic, hydrocarbon-based chain comprising from 1 to 100 carbon atoms, optionally interrupted with a heteroatom chosen from N, O, S and P.

$R_1$ preferably denotes a $C_1$-$C_{100}$ alkylene group, better still a propylene group, $R_2$ denotes an alkyl group containing from 1 to 6 carbon atoms or an alkoxy group containing from 1 to 6 carbon atoms.

$R_2$ preferably denotes a methyl group or a methoxy group.

n ranges from 0 to 132, and $n_1$ ranges from 1 to 132 m ranges from 1 to 132.

Preferably, the functionalized silicone(s) used in the present invention is or are chosen from the silicones of formula (XXIV).

As functionalized silicones used in the present invention, mention may be made of the mercaptosiloxane in which the mercapto functions are at the chain ends, sold by the company Shin-Etsu under the reference X-22-167B, and the mercaptosiloxane in which the mercapto functions are pendent, sold by the company Shin-Etsu under the reference KF-2001.

Preferably, the silicone functionalized with one or more mercapto groups is a mercaptosiloxane polymer of formula XXV in which the mercapto functions are pendent. According to a particular embodiment, the group R in formula XXV is a C3H6 alkylene group and the group R2 is a methyl radical.

The functionalized silicone(s) may be introduced into the composition(s) either in pure form or in the presence of one or more silicone-based or hydrocarbon-based solvents, or in the form of a latex.

Preferably, the silicone(s) (ii) is or are chosen from amino silicones.

The term "amino silicone" means any polyaminosiloxane, i.e. any polysiloxane comprising at least one primary, secondary or tertiary amine function or a quaternary ammonium group.

The amino silicone(s) used according to the present invention is or are chosen from:

(a) the compounds corresponding to formula (XVII) below:

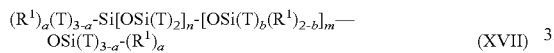
(XVII)

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and form to denote a number from 1 to 2000 and in particular from 1 to 10;

$R_1$ is a monovalent radical of formula —$C_qH2_qL$ in which q is a number from 2 to 8 and L is an amino group chosen from the following groups:

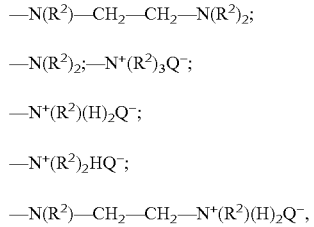

in which $R^2$ denotes a hydrogen atom, a phenyl, a benzyl or a saturated monovalent hydrocarbon-based radical, for example a $C_1$-$C_{20}$ alkyl radical, and $Q^-$ represents a halide ion, for instance fluoride, chloride, bromide or iodide.

In particular, the amino silicones corresponding to the definition of formula (XVII) are chosen from the compounds corresponding to formula (XVIII) below:

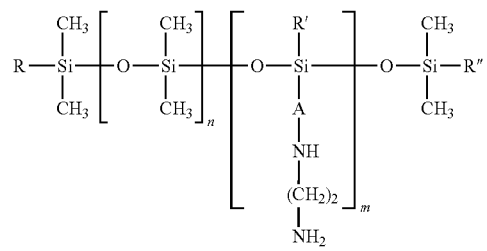
(XVIII)

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and the sum of which is between 1 and 2000.

According to a first possibility, R, R' and R", which may be identical or different, represent a $C_1$-$C_4$ alkyl or hydroxyl radical, A represents a $C_3$ alkylene radical and m and n are such that the weight-average molecular mass of the compound is between 5000 and 500 000 approximately. Compounds of this type are referred to in the CTFA dictionary as "amodimethicones".

According to a second possibility, R, R' and R", which may be identical or different, represent a $C_1$-$C_4$ alkoxy or hydroxyl radical, at least one of the R or R" radicals is an alkoxy radical and A represents a $C_3$ alkylene radical. The hydroxyl/alkoxy molar ratio is preferably between 0.2/1 and 0.4/1 and advantageously equal to 0.3/1. Moreover, m and n are such that the weight-average molecular mass of the compound is between 2000 and $10^6$. More particularly, n is between 0 and 999 and m is between 1 and 1000, the sum of n and m being between 1 and 1000.

In this category of compounds, mention may be made, inter alia, of the product Belsil® ADM 652 sold by Wacker.

According to a third possibility, R and R", which are different, represent a $C_1$-$C_4$ alkoxy or hydroxyl radical, at least one of the R and R" radicals is an alkoxy radical, R' represents a methyl radical and A represents a $C_3$ alkylene radical. The hydroxyl/alkoxy mole ratio is preferably between 1/0.8 and 1/1.1 and advantageously is equal to 1/0.95. Moreover, m and n are such that the weight-average molecular mass of the compound is between 2000 and 200 000. More particularly, n is between 0 and 999 and m is between 1 and 1000, the sum of n and m being between 1 and 1000.

More particularly, mention may be made of the product Fluid WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular mass of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

It is noted that the molecular mass of these silicones is determined by gel permeation chromatography (room temperature, polystyrene standard, μ styragem columns, eluent THF, flow rate of 1 mm/minute, 200 μl of a solution containing 0.5% by weight of silicone in THF are injected, and detection is performed by refractometry and UV-metry).

A product corresponding to the definition of formula (VI) is in particular the polymer known in the CTFA dictionary (7th edition, 1997) as "trimethylsilyl amodimethicone", corresponding to formula (XIX) below:

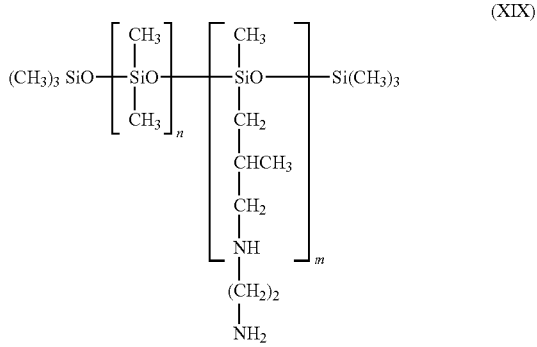

in which n and m have the meanings given above in accordance with formula (XVIII).

Such compounds are described, for example, in EP 0095238; a compound of formula (XIX) is sold, for example, under the name Q2-8220 by the company OSI.

(b) the compounds corresponding to formula (XX) below:

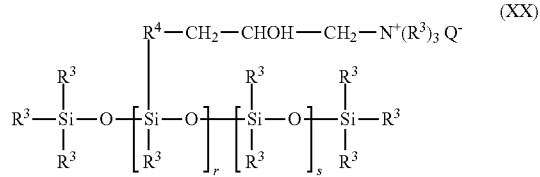

in which:

$R^3$ represents a monovalent $C_1$-$C_{18}$ hydrocarbon-based radical, and in particular a $C_1$-$C_{18}$ alkyl or $C_2$-$C_{18}$ alkenyl radical, for example methyl;

$R^4$ represents a divalent hydrocarbon-based radical, especially a $C_1$-$C_{18}$ alkylene radical or a divalent $C_1$-$C_{18}$, and for example $C_1$-$C_8$, alkyleneoxy radical;

$Q^-$ is a halide ion, especially chloride;

r represents a mean statistical value from 2 to 20 and in particular from 2 to 8;

s represents a mean statistical value from 20 to 200 and in particular from 20 to 50.

Such compounds are described more particularly in patent U.S. Pat. No. 4,185,087.

A compound falling within this class is the product sold by the company Union Carbide under the name Ucar Silicone ALE 56.

(c) the quaternary ammonium silicones of formula (XXI):

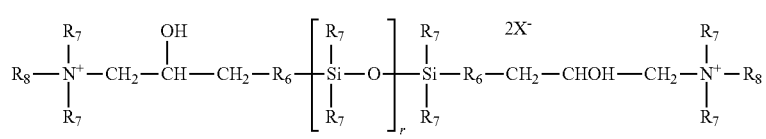

in which:

$R_7$, which may be identical or different, represents a monovalent hydrocarbon-based radical containing from 1 to 18 carbon atoms, and in particular a $C_1$-$C_{18}$ alkyl radical, a $C_2$-$C_{18}$ alkenyl radical or a ring containing 5 or 6 carbon atoms, for example methyl;

$R_6$ represents a divalent hydrocarbon-based radical, in particular a $C_1$-$C_{18}$ alkylene radical or a divalent $C_1$-$C_{18}$, for example $C_1$-$C_8$, alkyleneoxy radical linked to the Si via an SiC bond;

$R_8$, which may be identical or different, represents a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a —$R_6$—NHCOR$_7$ radical;

$X^-$ is an anion such as a halide ion, especially chloride, or an organic acid salt (acetate, etc.);

r represents a mean statistical value from 2 to 200 and in particular from 5 to 100.

These silicones are described, for example, in patent application EP-A 0 530 974.

d) the amino silicones of formula (XXII) below:

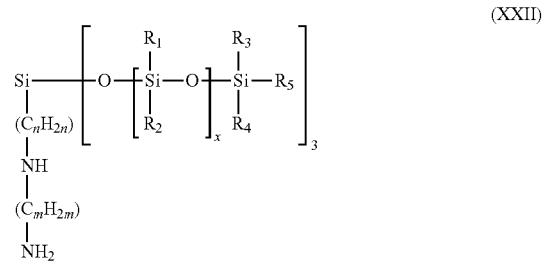

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and in which x is selected such that the amine number is between 0.01 and 1 meq/g.

According to one embodiment, the amino silicone is a silicone having the following formula in which R is a cetearyl radical:

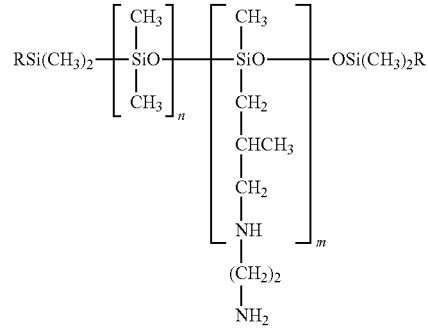

Preferably, the amino silicone(s) are non-quaternized amino silicones.

For the purposes of the present invention, the term "non-quaternized amino silicone" means an amino silicone not comprising a permanent cationic charge, i.e. quaternized ammonium groups.

In other words, the non-quaternized amino silicone(s) comprise in their structure at least one primary, secondary or tertiary amine function but do not comprise a quaternary ammonium function.

The silicone(s) functionalized with an amino or mercapto group may be present in the composition according to the invention in a content which may range from 0.1% to 10% by weight and preferably in a content ranging from 0.2% to 5% by weight relative to the total weight of the composition.

The vehicle of the composition according to the invention may comprise water and/or organic solvents. Organic solvents that may be mentioned include non-fatty alcohols such as ethyl alcohol, isopropyl alcohol, benzyl alcohol and phenylethyl alcohol, or polyols or polyol ethers, for instance glycerol, ethylene glycol monomethyl, monoethyl or monobutyl ether, propylene glycol or ethers thereof, for instance propylene glycol monomethyl ether, butylene glycol, dipropylene glycol, and also diethylene glycol alkyl ethers, for instance diethylene glycol monoethyl ether or monobutyl ether.

The organic solvent may be a fatty substance, which is preferably liquid. The liquid fatty substances preferably have a viscosity of less than or equal to 2 Pa·s, better still less than or equal to 1 Pa·s and even better still less than or equal to 0.1 Pa·s at a temperature of 25° C. and at a shear rate of 1 s$^{-1}$.

These fatty substances may be chosen from hydrocarbons composed solely of carbon and hydrogen atoms, fatty alcohols, for example
- linear or branched, optionally cyclic, $C_6$-$C_{16}$ alkanes. Examples that may be mentioned include hexane, undecane, dodecane, tridecane, and isoparaffins, for instance isohexadecane, isododecane and isodecane,
- linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as the product sold under the brand name Parleam® by the company NOF Corporation, and squalane,
- saturated liquid fatty alcohols chosen from octyldodecanol, isostearyl alcohol and 2-hexyldecanol.

The medium of the composition according to the invention may be a dispersed medium, especially dispersed in isododecane, an emulsion in water or an ethanol/water mixture.

The composition used according to the invention may be, independently of each other, in the form of a lotion, a gel, a mousse, a cream or a paste.

According to one embodiment, the composition according to the invention comprises one or more acrylate-functionalized silicone polymers and one or more silicones functionalized with one or more mercapto groups.

According to another embodiment, the composition according to the invention comprises one or more acrylate-functionalized silicone polymers and one or more amino silicones.

According to another embodiment, the composition according to the invention comprises one or more acrylate-functionalized silicone polymers, one or more silicones functionalized with one or more mercapto groups and one or more amino silicones.

Preferably, the composition according to the invention comprises one or more acrylate-functionalized silicone polymers and one or more silicones functionalized with one or more mercapto groups.

More preferentially, the composition according to the invention comprises (i) one or more acrylate-functionalized polymers chosen from acrylate-functionalized silicone copolymers obtained by polymerization from a mixture of monomers comprising at least one monomer of formula (I) or (II) and at least one dimethylsiloxane monomer and (ii) one or more functionalized silicones chosen from the silicones of formula (XXIV).

Even more preferentially, the acrylate-functionalized silicone copolymers are obtained by polymerization from a mixture of monomers comprising at least one monomer of formula (III).

The present invention also relates to the use of said composition for conditioning keratin fibres, in particular human keratin fibres such as the hair.

A subject of the invention is also a cosmetic process for treating keratin fibres, in particular human keratin fibres such as the hair, in which said fibres are treated with one or more compositions containing, taken together or separately in said composition(s), the following ingredients:
- one or more acrylate-functionalized polymers,
- one or more silicones chosen from silicones functionalized with one or more mercapto groups, amino silicones, and mixtures thereof.

The acrylate-functionalized polymer(s) and the functionalized silicones are as defined previously.

Preferably, the acrylate-functionalized polymer(s) is or are chosen from acrylate-functionalized silicone polymers, in particular acrylate-functionalized silicone copolymers.

Preferably, the process according to the invention comprises a step of applying to said fibres a composition comprising one or more acrylate-functionalized polymers and one or more silicones chosen from silicones functionalized with one or more mercapto groups, amino silicones, and mixtures thereof.

Alternatively, the process according to the invention comprises (a) a step of applying to said fibres a composition comprising one or more acrylate-functionalized polymers and (b) a step of applying to said fibres a composition comprising one or more silicones chosen from silicones functionalized with one or more mercapto groups, amino silicones, and mixtures thereof.

According to this alternative, step (a) may be performed before step (b) or vice versa.

The leave-on time of the composition or of each of the compositions defined above may be between 3 minutes and 1 hour.

The treatment process according to the invention may or may not be rinsed out.

The keratin fibres may be heated in the course of the process according to the invention at least to a temperature ranging from 40° C. to 210° C.

Preferably, the keratin fibres are heated after the application of the acrylate-functionalized polymer(s) and of the functionalized silicone(s).

According to one embodiment, the process according to the invention comprises:
(a) a step of applying to said fibres a composition comprising one or more acrylate-functionalized polymers, and
(b) a step of applying to said fibres a composition comprising one or more silicones chosen from silicones functionalized with one or more mercapto groups, amino silicones, and mixtures thereof, and
(c) at least one step of heating the keratin fibres to a temperature ranging from 40° C. to 210° C. performed after steps (a) and (b).

In accordance with this embodiment, the process according to the invention may comprise two steps of heating of the keratin fibres.

According to one embodiment, the process comprises a step of heating the keratin fibres to a temperature ranging from 40° C. to 60° C. and a step of heating the keratin fibres to a temperature ranging from 100° C. to 210° C. by means of a heat source.

In practice, this operation may be performed using a hairstyling hood, a hairdryer, a round or flat iron, an infrared ray dispenser or other heating appliances.

Preferably, the heat source is a straightening iron.

The process according to the invention may comprise a step of photochemical treatment of the keratin fibres in replacement for or in addition to the heating step as described previously.

Preferably, the photochemical treatment step is performed using a photoinitiator in an amount ranging from 1 to 20% by weight relative to the acrylate-functionalized polymer, especially the acrylate-functionalized silicone polymer.

More preferentially, the photoinitiator is 2,2-dimethoxy-2-phenylacetophenone.

According to a particular embodiment, the photoinitiator is a photoinitiator for UV.

The invention also relates to a multi-compartment device comprising a first compartment containing a composition comprising one or more acrylate-functionalized polymers and a second compartment containing one or more silicones chosen from silicones functionalized with one or more mercapto groups, amino silicones, and mixtures thereof.

Preferably, the device comprises a first compartment containing a composition comprising one or more acrylate-functionalized silicone polymers and a second compartment containing one or more silicones chosen from silicones functionalized with one or more mercapto groups, amino silicones, and mixtures thereof.

More preferentially, the device comprises a first compartment containing a composition comprising one or more acrylate-functionalized silicone polymers and a second compartment containing one or more silicones chosen from silicones functionalized with one or more mercapto groups.

Alternatively, the device comprises a first compartment containing a composition comprising one or more acrylate-functionalized silicone polymers and a second compartment containing one or more silicones chosen from silicones functionalized with one or more amino groups.

Also alternatively, the device comprises a first compartment containing a composition comprising one or more acrylate-functionalized silicone polymers and a second compartment containing one or more silicones chosen from silicones functionalized with one or more amino groups and silicones functionalized with one or more mercapto groups.

The following examples are given by way of illustration of the present invention.

EXAMPLE

I. Locks

The locks of hair were treated with the ingredients indicated in the table below:

| Locks | Ingredients |
|---|---|
| 1 | 100% isododecane |
| 2 | Silicone functionalized with mercapto groups[1] at 1% by weight in isododecane |
| 3 | Acrylate-functionalized silicone polymer[2] at 1% by weight in isododecane |
| 4 | Silicone functionalized with mercapto groups[1] at 0.75% by weight and acrylate-functionalized silicone polymer[2] at 0.25% in isododecane |
| 5 | Silicone functionalized with mercapto groups[1] at 0.25% by weight and acrylate-functionalized silicone polymer[2] at 0.75% by weight in isododecane |
| 6 | Silicone functionalized with mercapto groups[1] at 0.5% by weight and acrylate-functionalized silicone polymer[2] at 0.5% by weight in isododecane |
| 7 | Silicone functionalized with mercapto groups[1] at 0.5% by weight and acrylate-functionalized silicone polymer[2] at 0.5% by weight in isododecane |
| 8 | Silicone functionalized with mercapto groups[1] at 0.5% by weight, acrylate-functionalized silicone polymer[2] at 0.5% by weight, bis-cetearyl amodimethicone at 0.25% by weight, and ethyl-(2,4,6-trimethylbenzoyl)phenylphosphinate at 0.05% by weight in isopropyl myristate |
| 9 | Silicone functionalized with mercapto groups[1] at 0.5% by weight, acrylate-functionalized silicone polymer[2] at 0.5% by weight, bis-cetearyl amodimethicone at 0.25% by weight, and ethyl-(2,4,6-trimethylbenzoyl)phenylphosphinate at 0.05% by weight in isopropyl myristate |

[1] sold under the name KF2001 by the company Shin-Etsu (formula XXV with R1 = $C_3H_6$ and R2 = $CH_3$)
[2] sold under the name UMS 182 by the company Gelest (formula (III))

II. Procedure 2.1. Procedure—Application to the Locks

The compositions described in the table above are applied to locks 1 to 9 on each side with a brush.

Locks 1 to 6 are heated for a time of 30 minutes at a temperature of 50° C. and lock 7 is heated for a time of one hour at a temperature of 50° C. on a hotplate in a closed heating bag.

A straightening iron is then applied to each of the locks 1 to 6 by making continuous passes along the locks.

The locks are left to stand at room temperature for a time of 24 hours before performing a first sensory evaluation of the disentangling (measurement T0).

Lock 8 is placed under the exposure of a UV lamp ($\lambda$=365 nm, 100 Watts) for 5 minutes, then the lock is left to stand at room temperature for a time of 24 hours before performing a first sensory evaluation of the disentangling (measurement T0).

Lock 9 is placed under the exposure of a LED lamp (17 Watts) for 10 minutes on each side, then the lock is left to stand at room temperature for a time of 24 hours before performing a first sensory evaluation of the disentangling (measurement T0).

2.2. Evaluation of the Feel and of the Disentangling

After drying, disentangling tests with a comb were performed after immersion for 10 seconds in water, by passing a plastic comb through five times.

2.3. Procedure—Shampoo Resistance

Shampoo is applied to each of the locks, at a rate of 1 g per 2.8 g of locks, and the locks are then massaged for a time of 10 seconds. The shampoo is left on for a time of 3 minutes, before rinsing with water at a temperature of 37° C., 10 passes being performed. The lock is then dried.

This protocol is repeated five times and a second sensory evaluation of the disentangling is performed (measurement T5).

| Locks | T0 Disentangling | T5 Disentangling |
|---|---|---|
| 1 | − | − |
| 2 | + | − |
| 3 | + | − |
| 4 | ++ | ++ |
| 5 | ++ | ++ |
| 6 | ++ | ++ |
| 7 | + | ++ |
| 8 | ++ | + |
| 9 | ++ | ++ |

It is found that the compositions according to the invention lead to an improvement in the disentangling.

The invention claimed is:

1. Composition comprising:
one or more acrylate-functionalized silicone polymers of formula (I) or (II) below:

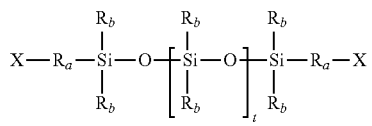

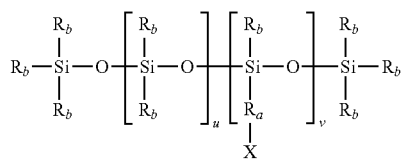

in which:
$R_a$ denotes a saturated or unsaturated hydrocarbon-based chain comprising from 1 to 100 carbon atoms that is linear, branched, or cyclic,
$R_b$ denotes an alkyl group containing from 1 to 6 carbon atoms or an alkoxy group containing from 1 to 6 carbon atoms,
t ranges from 0 to 132,
u ranges from 1 to 132,
v ranges from 1 to 132, and
X represents an acrylate-functionalized group; and
(ii) one or more silicones chosen from silicones functionalized with one or more mercapto groups, amino silicones, and mixtures thereof.

2. Composition according to claim 1, characterized in that the acrylate-functionalized silicone polymer(s) is or are of formula (III) below:

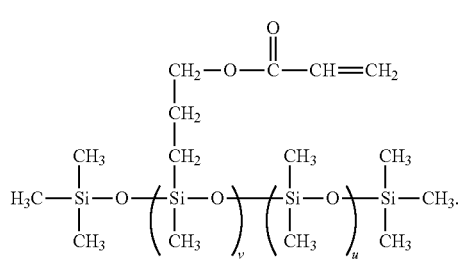

3. Composition according to claim 1, characterized in that the acrylate-functionalized silicone polymer(s) is or are chosen from silicone copolymers of acrylate and of dimethylpolysiloxane.

4. Composition according to claim 1, characterized in that the silicone(s) functionalized with one or more mercapto groups is or are chosen from the compounds of the following formulae:

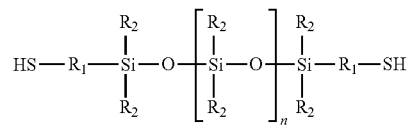

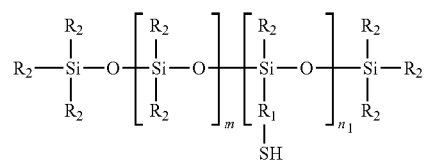

in which
$R_1$ denotes a saturated or unsaturated hydrocarbon-based chain comprising from 1 to 100 carbon atoms that is linear, branched, or cyclic
$R_2$ denotes an alkyl group containing from 1 to 6 carbon atoms or an alkoxy group containing from 1 to 6 carbon atoms,
n ranges from 0 to 132,
$n_1$ ranges from 1 to 132, and
m ranges from 1 to 132.

5. Composition according to claim 1, characterized in that the amino silicone(s) is or are chosen from:
(a) the compounds corresponding to formula (XVII) below:

$$(R^1)_a(T)_{3-a}\text{-Si}[OSi(T)_2]_n\text{-}[OSi(T)_b(R^1)_{2-b}]_m\text{—}OSi(T)_{3-a}\text{-}(R^1)_a \quad (XVII)$$

in which:
T is a hydrogen atom or a phenyl, hydroxyl (—OH) or $C_1$-$C_8$ alkyl radical, or a $C_1$-$C_8$ alkoxy,
a denotes the number 0 or an integer from 1 to 3,
b denotes 0 or 1,
m and n are numbers such that the sum (n+m) ranges from 1 to 2000 wherein n denotes a number from 0 to 1999, and m denotes a number from 1 to 2000;
$R^1$ is a monovalent radical of formula $CqH_2qL$ in which q is a number from 2 to 8 and L is an amino group chosen from the following groups:

—N($R^2$)—$CH_2$—$CH_2$—N($R^2$)$_2$;

—N($R^2$)$_2$;—$N^+(R^2)_3Q^-$;

—$N^+(R^2)(H)_2Q^-$;

—N+($R^2$)$_2$H$Q^-$;

—N($R^2$)—$CH_2$—$CH_2$—$N^+(R^2)(H)_2Q^-$, wherein $R^2$ denotes a hydrogen atom, a phenyl, a benzyl, or a saturated monovalent hydrocarbon-based radical, and Q represents a halide ion, (b) the compounds corresponding to formula (XX) below:

$$R^4-CH_2-CHOH-CH_2-N^+(R^3)_3 Q^- \\ R^3-Si(R^3)_2-O-[Si(R^3)_2-O]_r-[Si(R^3)(...)-O]_s-Si(R^3)_3 \tag{XX}$$

in which:
$R^3$ represents a monovalent $C_1$-$C_{18}$ hydrocarbon-based radical;
$R^4$ represents a divalent hydrocarbon-based radical;
$Q^-$ is a halide ion;
r represents a mean statistical value from 2 to 20;
s represents a mean statistical value from 20 to 200,
(c) the quaternary ammonium silicones of formula (XXI):

$$R_8-N^+(R_7)_2-CH_2-CH(OH)-CH_2-R_6-[Si(R_7)_2-O]_r-Si(R_7)_2-R_6-CH_2-CHOH-CH_2-N^+(R_7)_2-R_8 \quad 2X^- \tag{XXI}$$

in which:
$R_7$, which may be identical or different, represents a monovalent hydrocarbon-based radical containing from 1 to 18 carbon atoms;
$R_6$ represents a divalent hydrocarbon-based radical linked to the Si via a SiC bond;
$R_8$, which may be identical or different, represents a hydrogen atom, a monovalent hydrocarbon-based radical containing from 1 to 18 carbon atoms;
$X^-$ is an anion such as a halide ion-or an organic acid salt;
r represents a mean statistical value from 2 to 200;
d) the amino silicones of formula (XXII) below:

$$\left[Si(C_nH_{2n})(NH)(C_mH_{2m})(NH_2)-[O-Si(R_1)(R_2)]-[O-Si(R_3)(R_4)]_x-R_5\right]_3 \tag{XXII}$$

in which:
$R_1$, $R_2$, $R_3$ and $R_4$, which may be identical or different, denote a $C_1$-$C_4$ alkyl radical or a phenyl group,
$R_5$ denotes a $C_1$-$C_4$ alkyl radical or a hydroxyl group,
n is an integer ranging from 1 to 5,
m is an integer ranging from 1 to 5,
and in which x is selected such that the amine number is between 0.01 and 1 meq/g.

6. Composition according to claim 5, characterized in that the amino silicone corresponding to formula (XVII) is chosen from the compounds corresponding to formula (XVIII) below:

$$R-Si(CH_3)_2-[O-Si(CH_3)_2]_n-[O-Si(R')(A-NH-(CH_2)_2-NH_2)]_m-O-Si(CH_3)_2-R'' \tag{XVIII}$$

in which R, R' and R", which may be identical or different, denote a $C_1$-$C_4$ alkyl radical; a $C_1$-$C_4$ alkoxy radical; or OH; A represents a linear or branched, $C_3$-$C_8$ alkylene radical; m and n are integers dependent on the molecular weight and the sum of which is between 1 and 2000.

7. Composition according to claim 5, characterized in that the amino silicone of formula (XVII) is the silicone known as "trimethylsilylamodimethicone", corresponding to formula (XIX) below:

$$(CH_3)_3SiO-[Si(CH_3)_2O]_n-[Si(CH_3)(CH_2CHCH_3CH_2NH(CH_2)_2NH_2)O]_m-Si(CH_3)_3 \tag{XIX}$$

in which m and n are integers that are dependent on the molecular weight and whose sum is between 1 and 2000.

8. Composition according to claim 1, characterized in that it comprises one or more acrylate-functionalized silicone polymers and one or more silicones functionalized with one or more mercapto groups.

9. Process for treating keratin fibres, in which said fibres are treated with one or more compositions containing the following ingredients, taken together or separately in said composition(s):

(i) one or more acrylate-functionalized silicone polymers of formula (I) or (II) below:

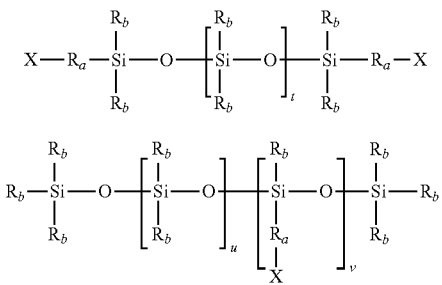

in which:

R$_a$ denotes a saturated or unsaturated hydrocarbon-based chain comprising from 1 to 100 carbon atoms that is linear, branched, or cyclic, R$_b$ denotes an alkyl group containing from 1 to 6 carbon atoms or an alkoxy group containing from 1 to 6 carbon atoms, t ranges from 0 to 132, u ranges from 1 to 132, v ranges from 1 to 132, and X represents an acrylate-functionalized group; and (ii) one or more silicones chosen from silicones functionalized with one or more mercapto groups, amino silicones, and mixtures thereof.

10. Process according to claim 9, characterized in that it comprises:

(a) a step of applying to said fibres a composition comprising one or more acrylate-functionalized silicone polymers of formula (I) or (II); and (b) a step of applying to said fibers a composition comprising one or more silicones chosen from silicones functionalized with one or more mercapto groups, amino silicones, and mixtures thereof.

11. Process according to claim 9, characterized in that it comprises at least one step of heating the keratin fibres to a temperature ranging from 40° C. to 210° C. after steps (a) and (b).

12. Process according to claim 9, characterized in that it comprises a step of photochemical treatment of keratin fibres using a photoinitiator.

13. Multi-compartment device comprising a first compartment containing a composition comprising one or more acrylate-functionalized silicone polymers as defined according to claim 1 and a second compartment containing one or more silicones chosen from silicones functionalized with one or more mercapto groups, amino silicones, and mixtures thereof.

* * * * *